US007753840B2

(12) United States Patent
Simionescu et al.

(10) Patent No.: US 7,753,840 B2
(45) Date of Patent: Jul. 13, 2010

(54) TISSUE MATERIAL PROCESS FOR FORMING BIOPROSTHESIS

(75) Inventors: Dan T. Simionescu, Central, SC (US); Narendra Vyavahare, Easley, SC (US)

(73) Assignee: Clemson University

(*) Notice: Subject to any disclaimer, the term of this patent is extended or adjusted under 35 U.S.C. 154(b) by 973 days.

(21) Appl. No.: 11/515,963

(22) Filed: Sep. 5, 2006

(65) Prior Publication Data

US 2007/0005132 A1    Jan. 4, 2007

Related U.S. Application Data

(63) Continuation of application No. 10/722,581, filed on Nov. 24, 2003, now Pat. No. 7,189,259.

(60) Provisional application No. 60/429,191, filed on Nov. 26, 2002.

(51) Int. Cl.
*A61F 2/24* (2006.01)

(52) U.S. Cl. .................. 600/36; 623/2.14; 623/2.42; 623/909

(58) Field of Classification Search ............. 623/23.72, 623/2.14, 2.42, 2.15, 2.16, 909; 600/36
See application file for complete search history.

(56) References Cited

U.S. PATENT DOCUMENTS

| | | | |
|---|---|---|---|
| 4,378,224 A | 3/1983 | Nimni et al. | |
| 4,400,833 A | 8/1983 | Kurland | |
| 4,588,579 A | 5/1986 | Bachhuber et al. | |
| 4,655,773 A | 4/1987 | Grassi | |
| 4,801,299 A | 1/1989 | Brendel et al. | |
| 5,252,344 A | 10/1993 | Shi | |
| 5,374,539 A | 12/1994 | Nimni et al. | |
| 5,397,353 A * | 3/1995 | Oliver et al. ............... 600/36 |
| 5,480,424 A * | 1/1996 | Cox ......................... 623/2.15 |
| 5,500,015 A * | 3/1996 | Deac ......................... 606/167 |
| 5,512,291 A | 4/1996 | Li | |
| 5,716,370 A | 2/1998 | Williamson, IV et al. | |
| 5,834,449 A | 11/1998 | Thompson et al. | |
| 5,855,620 A * | 1/1999 | Bishopric et al. ........... 128/898 |

(Continued)

FOREIGN PATENT DOCUMENTS

WO    WO 01/21228    3/2001

OTHER PUBLICATIONS

Narendra Vyavahare, et al., "Mechanisms of bioprosthetic heart valve failure: Fatigue causes collagen denaturation and glycosaminoglycan loss", Journal of Biomedical Materials Reasearch Part A, vol. 46, Issue 1, pp. 44-50, (1999).*

(Continued)

*Primary Examiner*—Paul Prebilic
(74) *Attorney, Agent, or Firm*—Dority & Manning, P.A.

(57) ABSTRACT

A biomaterial useful for bioprostheses such as bioprosthetic heart valves is provided in which the fixed tissue has improved elastic properties. The high elastin-containing biomaterial is further characterized by having anisotropic properties wherein the biological material has a greater stiffness in one direction and a greater elasticity in a cross direction. For instance, the biological material has an elastin content of about 30% by weight. In one embodiment, the biological material is vena cava tissue.

8 Claims, 4 Drawing Sheets

U.S. PATENT DOCUMENTS

| | | | |
|---|---|---|---|
| 5,899,937 A | 5/1999 | Goldstein et al. | |
| 5,990,379 A | 11/1999 | Gregory | |
| 6,001,126 A | 12/1999 | Nguyen-Thien-Nhon | |
| 6,071,541 A | 6/2000 | Murad | |
| 6,102,944 A | 8/2000 | Huynh et al. | |
| 6,110,206 A | 8/2000 | Stone | |
| 6,197,053 B1 | 3/2001 | Cosgrove et al. | |
| 6,210,957 B1 | 4/2001 | Carpentier et al. | |
| 6,214,054 B1 | 4/2001 | Cunanan et al. | |
| 6,228,387 B1 | 5/2001 | Borod | |
| 6,245,105 B1 | 6/2001 | Nguyen et al. | |
| 6,267,834 B1 | 7/2001 | Shannon et al. | |
| 6,278,079 B1 | 8/2001 | McIntyre et al. | |
| 6,328,763 B1 * | 12/2001 | Love et al. | 623/2.15 |
| 6,331,319 B1 | 12/2001 | Badylak et al. | |
| 6,338,740 B1 | 1/2002 | Carpentier | |
| 6,342,070 B1 | 1/2002 | Nguyen-Thien-Nhon | |
| 6,378,221 B1 | 4/2002 | Ekholm, Jr. et al. | |
| 6,391,538 B1 * | 5/2002 | Vyavahare et al. | 435/1.1 |
| 6,402,780 B2 | 6/2002 | Williamson, IV et al. | |
| 6,409,758 B2 | 6/2002 | Stobie et al. | |
| 6,413,275 B1 | 7/2002 | Nguyen et al. | |
| 6,416,547 B1 | 7/2002 | Erickson et al. | |
| 6,444,222 B1 | 9/2002 | Asculai et al. | |
| 6,454,799 B1 | 9/2002 | Schreck | |
| 6,457,827 B1 | 10/2002 | Groaser et al. | |
| 6,458,155 B1 | 10/2002 | Van Nguyen et al. | |
| 6,461,382 B1 | 10/2002 | Cao | |
| 6,479,079 B1 | 11/2002 | Pathak et al. | |
| 6,506,197 B1 | 1/2003 | Rollero et al. | |
| 6,532,388 B1 | 3/2003 | Hill et al. | |
| 6,539,984 B2 | 4/2003 | Lam | |
| 6,547,827 B2 | 4/2003 | Carpentier et al. | |
| 6,558,418 B2 | 5/2003 | Carpentier et al. | |
| 6,561,970 B1 | 5/2003 | Carpentier et al. | |
| 6,579,538 B1 | 6/2003 | Spievack | |
| 6,585,766 B1 | 7/2003 | Huynh et al. | |
| 6,626,939 B1 | 9/2003 | Burnside et al. | |
| 6,645,764 B1 | 11/2003 | Adkisson | |
| 6,824,970 B2 | 11/2004 | Vyavahare et al. | |
| 6,861,211 B2 | 3/2005 | Levy et al. | |
| 7,189,259 B2 * | 3/2007 | Simionescu et al. | 623/2.42 |
| 7,252,834 B2 | 8/2007 | Vyavahare et al. | |
| 2002/0095994 A1 | 7/2002 | Vesely et al. | |
| 2003/0078659 A1 | 4/2003 | Yang | |
| 2003/0130729 A1 * | 7/2003 | Paniagua et al. | 623/2.11 |
| 2003/0138950 A1 | 7/2003 | McAllister et al. | |
| 2004/0153145 A1 | 8/2004 | Simionescu et al. | |
| 2004/0258729 A1 * | 12/2004 | Czernuszka et al. | 424/426 |
| 2005/0021026 A1 | 1/2005 | Baily | |
| 2005/0065430 A1 | 3/2005 | Wiethoff et al. | |
| 2006/0240066 A1 | 10/2006 | Vyavahare et al. | |
| 2006/0246584 A1 * | 11/2006 | Covelli | 435/396 |

OTHER PUBLICATIONS

Article—*Aluminum Chloride Pretreatment of Elastin Inhibits Elastolysis by Matrix Metalloproteinases and Leads to Inhibition of Elastin-Oriented Calcification*, Michael Bailey et al., The American Journal of Pathology, vol. 159, 2001, pp. 1981-1986, ajp.amjpathol.org, Nov. 17, 2003.

Paper from Cedars-Sinai Medical Center entitled "Cedars-Sinai Medical Center Prosthetic Heart Valve Information", 37 pages.

Abstract of Article—*Calcification of bovine pericardium used in cardiac valve bioprostheses. Implications for the mechanisms of bioprosthetic tissue mineralization*, Schoen et al., American Journal of Pathology, vol. 123, 1986, pp. 134-145.

Article—*Biochemical characterization of individual normal, floppy and rheumatic human mitral valves*, Lis et al., Biochcm. J., vol. 244, 1987, pp. 597-603.

Article—*Construction of varying porous structures in acellular bovine pericardia as a tissue-engineering extracellular matrix*, Wei et al., Biomaterials, vol. 26, 2005, pp. 1905-1913.

Article—*Content of Collagen, Elastin, and Water in Walls of the Internal Saphenous Vein in Man*, Svejcar et al., Circulation Research, vol. XI, Aug. 1962, pp. 296-300.

Article—*The association between venous structural alterations and biomechanical weakness in patients with abdominal aortic aneurysms*, Goodall et al., Journal of Vascular Surgery, vol. 35, No. 5, pp. 937-942 with appendix of 2 pages.

\* cited by examiner

TISSUE MATERIAL PROCESS FOR FORMING BIOPROSTHESIS

CROSS REFERENCE TO RELATED APPLICATIONS

This application is a continuation application of U.S. patent application Ser. No. 10/722,581 having a filing date of Nov. 24, 2003 (now U.S. Pat. No. 7,189,259), which claims benefit to U.S. Provisional Application Ser. No. 60/429,191 filed Nov. 26, 2002.

FEDERALLY SPONSORED RESEARCH AND DEVELOPMENT

The United States Government may have rights in this invention pursuant to Grant No. HL 61652 between Clemson University and the National Institutes of Health.

BACKGROUND OF THE INVENTION

Prosthetic heart valves are used to replace damaged or diseased heart valves. Prosthetic heart valves may be used to replace a heart's natural valves including aortic, mitral, and pulmonary valves. The predominant types of prosthetic heart valves are either mechanical valves or bioprosthetic valves. Bioprosthetic valves include allograft valves, which include biomaterial supplied from human cadavers; autologous valves, which include biomaterial supplied from the individual receiving the valve; and xenograft valves, which include biomaterial obtained from non-human biological sources including pigs, cows or other animals.

Presently, mechanical valves have the longest durability of available replacement heart valves. However, implantation of a mechanical valve requires a recipient to be prescribed anti-coagulants to prevent formation of blood clots. Unfortunately, continuous use of anticoagulants can be dangerous, as it greatly increases the user's risk of serious hemorrhage. In addition, a mechanical valve can often be audible to the recipient and may fail without warning, which can result in serious consequences, even death.

The use of bioprosthetic heart valves (BHVs) in valve replacement procedures is often preferred as BHVs do not require ongoing patient treatment with anticoagulants. Allograft transplants have been quite effective, with good compatibility and blood flow characteristics in the recipients. However, the availability of human valves for transplantation continues to decline as a percentage of cardiac surgeries performed each year. As such, the choice of xenograft materials for use in replacement BHVs is becoming more common.

Both xenografts and allografts require that the graft biomaterial be chemically fixed, or cross-linked, prior to use, in order to render the biomaterial non-antigenic as well as improve resistance to degradation. Currently, glutaraldehyde fixation of xenograft or allograft biomaterial is commonly used. Glutaraldehyde fixation forms covalent cross-links between free amines in the tissue proteins. As a result, the tissue is less susceptible to adverse immune reactions by the patient. Fixation is also believed to improve the valve durability by making the tissue stronger and less susceptible to enzymatic degradation.

One disadvantage of current xenograft materials is poor durability. At present, conventional xenograft valves require replacement within five to ten years of the original repair. This is at least in part due to the fact that xenografts, particularly those chemically fixed with glutaraldehyde, are stiffer and less pliable than the recipient's original valve. As a consequence of the increased stiffness, the periodic opening and closing of the valve leads to material fatigue of the bioprosthetic replacement tissue. In addition, the recipient's heart will be required to work harder to overcome the stiffness of the bioprosthetic valve as compared to the exertion required for the original valve to function. As the material integrity of the xenograft valve is lessened over time, the efficiency of the valve operation also decreases. Additionally, fatigue and mechanical degradation of the xenograft valve is associated with increased calcification of the valve. The calcification causes additional stiffening which further degrades the physical and biological integrity of the valve.

One form of a conventional bioprosthetic tissue valve comprises a stent which may be in the form of a rigid, annular ring portion onto which separate leaflets of fixed bovine or porcine pericardium are attached. The leaflets are sewn together so as to provide a movement similar to that of an actual heart valve. Unfortunately, due to the heterogenic nature of the pericardium, the pericardium source material used to form the BHV leaflets can have notable variations in physical properties, even when harvested from the same pericardial sac. For example, Simionescu et al. (*Mapping of Glutaraldehyde-treated Bovine Pericardium and Tissue Selection for Bio-Prosthetic Heart Valves, Journal of Biomedical Materials Research*, 27(6), 697, 1993, which is incorporated herein by reference) discusses differences in individual pericardium sacs with respect to fiber orientation, suture holding power, and thickness. In an effort to form more homogeneous bioprosthetic heart valve leaflets, it has been suggested that individual heart valve leaflets be tested and evaluated prior to BHV formation so as to use leaflets having similar properties, such as similar deflection values (see, for example, U.S. Pat. No. 6,413,275 B1, which is incorporated herein by reference).

Despite these advances in addressing the needs for longer lasting and better performing BHVs, there remains room for variation and improvement within the art.

SUMMARY OF THE INVENTION

The present invention is generally directed to improved bioprostheses and methods for forming the improved bioprostheses. In accordance with the invention, a bioprosthesis can include a tissue having an elastin content of at least about 10% by weight of the tissue and a support material attached to the tissue. In one embodiment, the elastin content of the tissue can be higher, for instance at least about 30% by weight of the tissue.

In one embodiment, the bioprostheses of the invention can include an anisotropic tissue, for example, an anisotropic tissue exhibiting greater stiffness in a first direction and greater elasticity in a second direction.

In one particular embodiment of the invention, the tissue can be vena cava tissue, for example, porcine vena cava tissue.

The support materials used in conjunction with the disclosed tissue can be any bioprosthetic support materials as are generally known in the art, for instance, stents and/or suture rings.

Bioprostheses that can be formed utilizing the disclosed tissues can include bioprosthetic heart valves. For example, the bioprostheses of the invention can include tricuspid heart valves and bicuspid heart valves.

The present invention is also directed to methods for forming the disclosed bioprostheses. The methods generally include providing tissue in a flat orientation and excising a portion of the flat tissue for attachment to a support material.

The portion of the flat tissue that is excised from the flat sheet can generally have the desired shape to be attached in the bioprosthesis, for example, the shape of an individual tricuspid or bicuspid valve leaflet.

In one embodiment, wherein the tissue used in the bioprosthesis is an anisotropic material, the tissue portion that is excised from the flat tissue can be oriented so as to improve the mechanical properties of the bioprosthesis. For example, in one embodiment, the excised portion can have the general shape of a heart valve leaflet. In this particular embodiment, the direction of greater elasticity of the anisotropic material can be substantially equivalent to the center-most radius of the leaflet as cut from the sheet.

In those embodiments wherein the tissue is vena cava tissue, the flat tissue sheet may be formed by opening a vena cava section with a longitudinal incision.

The present invention is also directed to methods of replacing damaged heart valves with bioprosthetic heart valves including the tissue as herein disclosed.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying drawings in which.

DETAILED DESCRIPTION OF THE INVENTION

Figure 1:
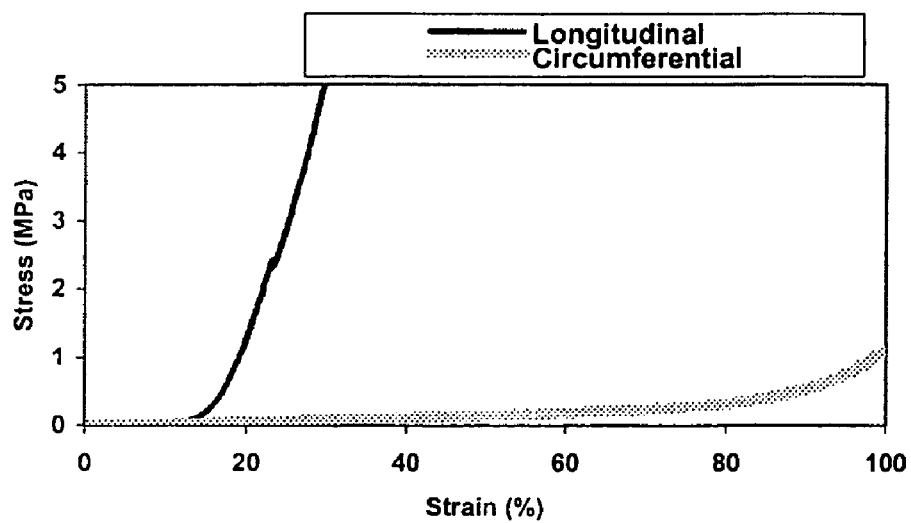
FIG. 1 is a graph setting forth longitudinal and circumferential stress and strain properties of glutaraldehyde-fixed porcine vena cava tissue as may be used in accordance with the present invention.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

As used herein the term "bioprosthesis" includes any prosthesis which is derived in whole or in part from human, animal, or other organic tissue and which can be implanted into a human or an animal. Accordingly, the term "bioprosthesis" includes cardiac prostheses such as heart valves, other replacement heart components, and cardiac vascular grafts. In addition, the properties of the tissue described herein may also lend itself as a prosthetic material for use with other organs and tissue systems.

As used herein, the term "cross-link" refers generally to the process of forming bonds, e.g., covalent bonds, between free, active moieties on or within tissue or between a cross-linking agent or other compound which reacts with a reactive moiety of the tissue. It is generally recognized that in forming bioprostheses, it is desirable to leave as few active moieties within the biological tissue as possible. The resulting cross-linked tissue is considered "fixed."

As used herein, the term "fixed" in regard to tissue is defined to refer to tissue that is stabilized so as to be less antigenic and less susceptible to physical and biological degradation.

The term "tissue" is used as understood by those having skill in the art to include any natural or synthetic material derived from an organic source and which may be implanted in a mammal. While exemplary forms of a tissue are described herein, the term "tissue" is not limited to the exemplary embodiments but may include other types of tissues having properties similar to the exemplary tissue.

In general, the present invention is directed to improved bioprostheses utilizing tissue that exhibits improved physical characteristics over biomaterials utilized in the past. More specifically, it has been found that a tissue can be provided for use in a bioprosthesis that exhibits improved physical characteristics over materials used in the past, including xenograft, autologous, and allograft aortic cusp and pericardium derived biomaterials. According to the present invention, tissue having an elastin content greater than about 10% can be utilized to form a bioprosthesis. In one embodiment, the tissue can be an anisotropic material, that is, a material in which the measured characteristics of the material differ depending upon the direction of measurement. In one embodiment of the present invention, vena cava tissue can be utilized in forming a bioprosthesis.

The tissue of the present invention can generally be utilized in any of a number of bioprostheses. For instance, bioprostheses can be formed according to the present invention including any of a variety of cardiac bioprostheses that can serve to replace damaged sections of the cardiovascular system. For example, bioprosthetic heart valves, veins, or arteries can be formed. In general, the bioprostheses of the present invention can include the tissues herein discussed in conjunction with other support materials as are generally known in the art. For instance, bioprostheses according to the present invention can include the disclosed tissue in suitable combination with support materials such as wire forms, stents, suture rings, conduits, flanges, and the like.

In one embodiment, a bioprosthetic heart valve (BHV) can be formed including heart valve leaflets formed of the disclosed biomaterials and secured to a stent. Suitable stent materials can generally include stent materials as may generally be found in other known heart valves, including both mechanical and bioprosthetic heart valves. For example, in one embodiment, tissue leaflets according to the present invention can be attached to a flexible polymer stent formed of, for example, polypropylene, reinforced with a metal ring (such as, for example, a Haynes™ alloy no. 25 metal ring). In another embodiment of the invention, a polymer stent can be used including a polyester film support secured to a surgically acceptable metal ring such as an Elgiloy™ metal stiffener. Optionally, a stent may be formed of only polymeric materials, and not include any metals. Alternatively, the disclosed bioprosthesis can include a wire stent, such as an Elgiloy™ wire stent, or a titanium stent, which can be optionally covered with a material cover, such as, for example, Dacron™. In some embodiments, the valve can include a sewing or suture ring such as, for example, a polyester, Dacron™, or Teflon™ suture ring, as is generally known in the art. In yet another embodiment, the disclosed bioprosthesis can be a stentless heart valve. It should be clear, however, that these are exemplary materials, and the make-up of the support material in the disclosed bioprostheses is not critical to the disclosed invention.

The improved bioprostheses of the present invention can include tissue that can be xenograft, allograft, or even autologous graft materials. In general, suitable biomaterials can be provided by tissue culture techniques as are generally known in the art, and thus, such techniques need not be discussed in detail herein.

The tissues that can be used in the bioprostheses of the present invention can display improved properties of strength, durability, and elasticity. In one embodiment, the disclosed tissues can exhibit similar cross-link densities following fixation as previously known bioprosthetic tissue, while exhibiting greatly improved elasticity over these fixed materials. While not wishing to be bound by any particular theory, these improvements are believed to be due at least in part to the relative levels of collagen and elastin contained in the disclosed tissues.

Collagen is the fibrous protein constituent of connective tissue. Chemically, it is a triple helix formed of three extended protein chains that wrap around one another. In vivo, many rod-like collagen molecules are cross-linked together in the extracellular space to form unextendable collagen fibrils that have the tensile strength of steel.

Elastin is a protein similar to collagen in make-up and is the principal structural component of elastic fibers. Elastin polypeptide chains are cross-linked together to form rubber-like, elastic fibers. Unlike collagen, elastin molecules can uncoil into a more extended conformation when the fiber is stretched and will recoil spontaneously as soon as the stretching force is relaxed.

According to the present invention, bioprostheses are disclosed including tissues which have a greater elastin content than tissues used in similar bioprostheses in the past. In one embodiment, the tissues of the present invention can also have a lower collagen content than the tissues used in similar bioprostheses in the past. As such, the bioprostheses of the disclosed invention can exhibit improved physical characteristics, and in particular improved elasticity and durability.

For example, in one particular embodiment of the present invention, the bioprosthetic tissue can have three to four times greater elasticity than tissue derived from the pericardium of the same donor species. The greater extensibility of the tissue is believed to offer long-term benefits in terms of durability and resistance to mechanical degradation. The increase in mechanical durability is believed to provide additional attributes in terms of reducing the onset and amount of calcification which is frequently associated with bioprosthesis failure, and in particular, with BHV failure. Additionally, to the extent the more elastic tissue can be more resistant to mechanical damage and degradation, it is believed that greater resistance to biological degradation is also provided. Both the resistance to calcification and the resistance to biological degradation are believed to further enhance the longevity of implanted bioprostheses formed of the presently disclosed tissues.

In one embodiment, the bioprostheses of the present invention can include tissue having an elastin content greater than about 10% by weight. In another embodiment, the bioprostheses of the present invention can include tissue having an elastin content greater than about 30% by weight.

Collagen content can be proportional to the stiffness of the tissue which, as discussed above, can contribute to the lack of durability of a bioprosthesis. As such, in one embodiment, the disclosed tissues can have a lower collagen content than tissues utilized in the past in similar bioprostheses. For example, in one embodiment, the bioprostheses of the disclosed invention can include tissue having a collagen content less than about 50% by weight.

One preferred tissue suitable for use in the bioprostheses of the present invention can be provided from vena cava source material such as porcine, bovine or other large animal vena cava. In an alternative embodiment, vena cava tissue may be provided from allograft or autologous vena cava source material. While the examples below are described in reference to porcine inferior vena cava material, it is believed that superior vena cava material can also provide the benefits as noted below. Additionally, to the extent vena cava tissue derived from other animal species provide similar benefits, the scope of the present disclosure and claims should not be limited to vena cava material derived from any particular species.

Figure 5:
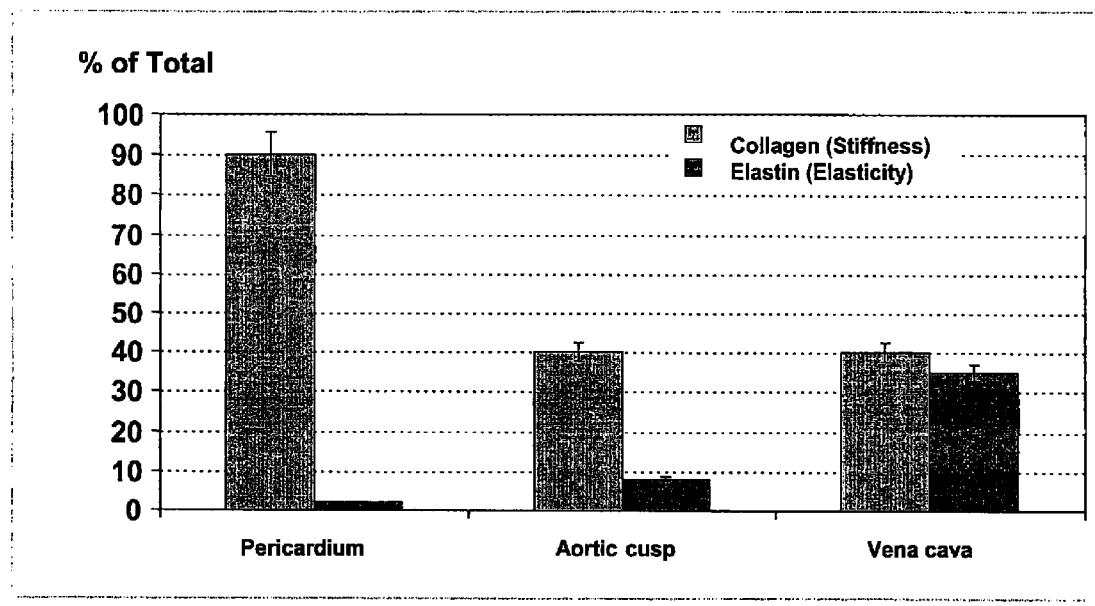
FIG. 5 is a graph indicating the relative composition of various BHV biological tissues.

The useful nature of the vena cava derived tissue is reflective of the molecular and structural composition of the vena cava source material. As seen in reference to FIG. 5, a comparison of elastin and collagen composition is provided for bovine pericardium, porcine aortic cusps, and porcine vena cava tissues. As seen, the vena cava material has only about 40% by weight collagen compared to a 90% value for pericardium. Additionally, the vena cava material has a much higher percentage of elastin. The increased elastin content for the vena cava tissues contributes to the improved properties of the resulting bioprosthesis.

In addition to increased elastin levels, in one embodiment, the tissue of the disclosed prostheses can display anisotropic properties. In general, anisotropic materials can display both great versatility and utility due to the variety of physical characteristics obtainable from the material through variation of orientation of the material. For example, anisotropic tissue can be oriented in the disclosed bioprostheses so as to exhibit a greater stiffness in one direction, preferably a direction requiring less movement from the tissue following implant, and a greater elasticity in a second direction which can be the direction in which motion of the tissue will generally be expected following implant. As such, even greater improvements in mechanical characteristics can be obtained in the bioprostheses prepared with the disclosed anisotropic materials. For example, test results have revealed that fixed vena cava tissue as provided herein can be extended up to about 200% in the longitudinal direction without breakage, and even farther in the circumferential direction.

Desirably, the tissue of the present invention can closely mimic the natural action and elasticity of the tissue in a healthy organ. In one embodiment of the invention, this mimicking effect can be maximized through optimal utilization of tissue exhibiting anisotropic characteristics. Utilization of tissue having anisotropic characteristics, such as, for example, anisotropic vena cava tissue, can allow the tissue to be positioned and oriented within a particular bioprosthesis so as to achieve enhanced mechanical performance as well as mimic the natural action of the healthy, original tissue.

For example, in one embodiment, the tissue of the present invention can be utilized in forming the individual leaflets of a BHV. In this embodiment, an anisotropic tissue leaflet can be oriented within the heart valve so as to provide increased elasticity in the radial direction and increased stiffness in the circumferential direction, as is found in undamaged heart valves. Increased elasticity in the radial direction can enhance the longevity and mechanical performance of the leaflet, specifically with regard to the repeating motion required of the leaflets in opening and closing the valve. Similarly, increased stiffness in the circumferential direction of the leaflets can help maintain the overall structure and shape of the valve over time. Thus, utilization of anisotropic tissue of the present invention can improve longevity of a BHV, thereby reducing the occurrence of subsequent surgery to repair a damaged or failing prosthesis.

In general, the tissue of the disclosed bioprostheses can be prepared from a substantially flat sheet. In one particular embodiment, a single flat sheet can have a size sufficient to excise all of the necessary portions of a single bioprosthesis. For instance, when forming a BHV according to the present invention, the flat sheet can be large enough such that all of the cusps for a single replacement heart valve can be cut from a single sheet, be it a tricuspid valve (e.g., an aortic or pulmonary valve) or a bicuspid valve (e.g., a mitral valve) that will be formed.

Figure 4:
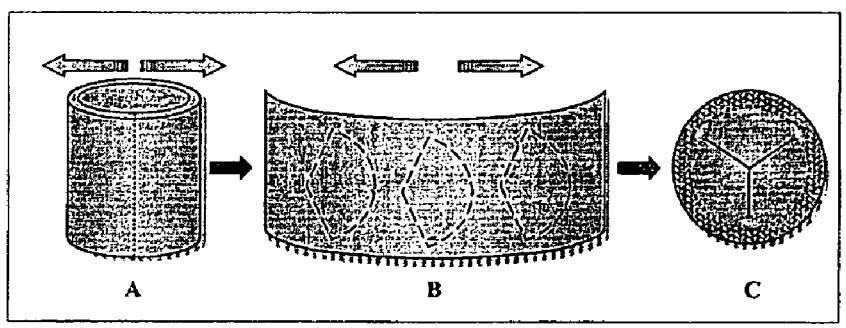
FIG. 4 is a schematic view showing one embodiment for obtaining a flat template of biomaterial from porcine vena cava and additionally setting forth one embodiment for the orientation of individual valve leaflets that may be attached onto a conventional 3-prong stent to create a porcine vena cava-based tricuspid BHV.

As best seen in reference to FIG. 4, harvested section "A" derived from vena cava may be opened using a longitudinal incision as seen by the dotted line. The opened vena cava tissue can be chemically fixed, such as using glutaraldehyde, as is generally known in the art or using any other suitable fixative agent such as, for example, a phenolic tannin fixative agent such as tannic acid, either alone or in combination with a glutaraldehyde fixative agent. Following fixation, the fixed tissue may then be manipulated to form a substantially flat sheet of tissue as seen in reference to "B" in FIG. 4. The tissue sheet seen in FIG. 4 "B" may then be used to provide portions of a bioprosthesis as indicated by the dashed lines. The portions, such as the illustrated leaflets, may then be used in any manner for which conventional tissue is used, such as, for example, pericardium tissue, with respect to valve replacements and related grafts. As seen in "C", on FIG. 4, the tissue portion can be sutured onto a 3-prong stent to provide a bioprosthetic heart valve.

It should be understood that, while illustrated in this particular embodiment as forming a tricuspid valve, the biomaterial of the present invention can alternatively be utilized in forming other valves and other bioprostheses.

In further reference to FIG. 4, the shaded arrows are used to designate the circumferential direction of the anisotropic vena cava tissue. As further discussed in the example section below, in the case of vena cava tissue, the circumferential direction exhibits the greatest elasticity. As seen in reference to FIG. 4, the circumferential direction of the original vein can be oriented to substantially equate with the radial direction of the excised leaflet; that is, with the circumferential direction of the vena cava tissue generally corresponding to the center-most radius of the excised leaflet. Thus, the leaflets may be excised from the biomaterial in an orientation that achieves maximum elasticity in a radial direction of each leaflet. In so doing, the anisotropic properties of the vena cava-derived biomaterial can be used to advantage to orient and mount the leaflets and supports so as to achieve improved mechanical properties, as discussed above.

Following formation of a bioprosthetic device according to the present invention, the device can be implanted by any surgical procedure as is generally known in the art. For example, a BHV including the tissue of the invention can be implanted in the heart of a person or an animal according to known surgical procedures such as, for example, procedures described in U.S. Pat. No. 6,532,388 to Hill et al., U.S. Pat. No. 6,506,197 to Rollero et al., and U.S. Pat. Nos. 6,402,780, 6,042,607, and 5,716,370 all to Williamson, IV et al., all of which are incorporated herein by reference. In general, such procedures include removal of a damaged cardiac valve, implantation of the new replacement valve in the cardiac valve annulus, and attachment of the BHV to the adjacent tissue.

Reference now will be made to exemplary embodiments of the invention set forth below. Each example is provided by way of explanation of the invention, not as a limitation of the invention. In fact, it will be apparent to those skilled in the art that various modifications and variations may be made of this invention without departing from the scope or spirit of the invention.

Example 1

Tissue Collection and Characterization

Porcine inferior vena cava was collected from a slaughterhouse and placed in ice-cold saline. The vena cava was manually cleaned of adherent tissues, followed by opening the veins using a longitudinal incision. After rinsing the vena cava material in fresh saline, the tissue was fixed for 7 days at room temperature in 0.6% glutaraldehyde (GA) prepared in 50 mM HEPES buffered saline at pH 7.4. The fixative was changed with fresh GA solution following an initial 24-hour fixation interval.

Glutaraldehyde fixed vena cava was cut with a template to obtain samples approximately 40 mm long and 5 mm wide. Six samples were obtained and examined in both a longitudinal direction (parallel to the axis of the blood flow) and in a circumferential direction (perpendicular to blood flow). Stress and strain tests were performed at room temperature on a Vitrodyne V-1000 mechanical tester (Lifeco Inc, Burlington, Vt.) equipped with a 10-pound load cell. Specimens were clamped onto serrated tester grips and initial tissue length and thickness were measured under a load of about 1 gram. Each specimen was subsequently extended until rupture under a constant extension rate of 6 mm/min. Data recordings for load (N) and percent extension in millimeters were acquired on a personal computer using an I/O interface. Stress/Strain profiles were generated by converting applied loads to Stress (N/tissue cross sectional area) and extension values to % Strain (100×Extended length-Initial length/Initial length). The resulting data is set forth in FIG. 1.

Example 2

Thermal Denaturation ($T_d$) Profiles Assessed by Differential Scanning Calorimetry (DSC)

Figure 2:
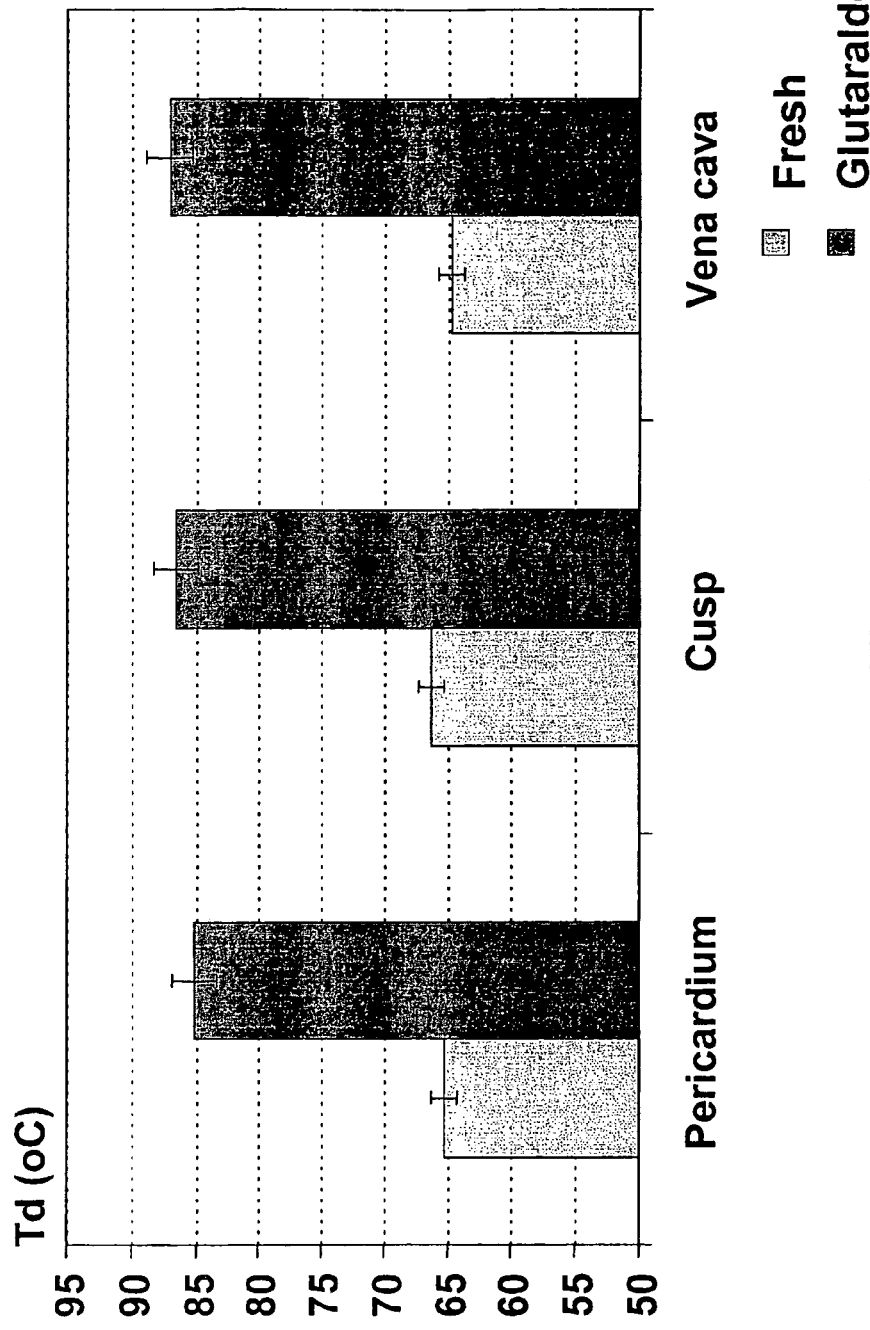
FIG. 2 is a graph indicating the thermal denaturation temperature of various xenograft materials before and after fixation in glutaraldehyde.

$T_d$ indicates the amount of energy absorbed by a sample. In the case of connective tissues, $T_d$ represents the temperature at which native collagen molecules unravel. This process leads to protein denaturation and is recorded as a peak maximum for three different tissues types in FIG. 2. Fresh, native tissues exhibit a $T_d$ of around 65° C., while chemically cross-linked tissues require a larger amount of heat to denature, and therefore their $T_d$ increases proportionally to the number of cross-links.

Porcine vena cava tissue (native and GA fixed, as described above) was rinsed in saline and 2 mm² samples were cut and hermetically sealed in Differential Scanning Calorimetry (DSC) aluminum pans. Samples were heated at a rate of 10° C./min, from 25° C. to 110° C. and the temperature of thermal denaturation ($T_d$) for each sample was recorded on a Perkin Elmer DSC 7 machine.

Fresh vena cava exhibited a $T_d$ of around 65° C., while chemical cross-linking with GA increased $T_d$ values to 87° C. (Table 1) indicative of a high degree of cross-linking. These values are similar to those reported in the literature for glutaraldehyde cross-linked bovine pericardium and aortic cusp tissues as set forth in Table 1 and illustrated graphically in FIG. 2.

TABLE 1

Thermal denaturation temperatures for glutaraldehyde fixed tissues used in bioprosthetic heart valves.

| | Tissue | | |
|---|---|---|---|
| | Porcine aortic cusp | Bovine pericardium | Porcine vena cava |
| Mean $T_d$ (° C.) +/− SEM | 86.9 +/− 1.3 | 86.8 +/− 0.63 | 87.02 +/− 0.19 |

(Values are not statistically different (P > 0.02))

The data indicate that fixation of vena cava with GA induces the formation of a large number of intermolecular cross-links and that the procedure outlined above yields a tissue biomaterial similar in cross-link density to tissues that are currently used in manufacturing of bioprosthetic heart valves.

Example 3

Comparison of Elastic Properties of Various Tissues

Figure 3A:
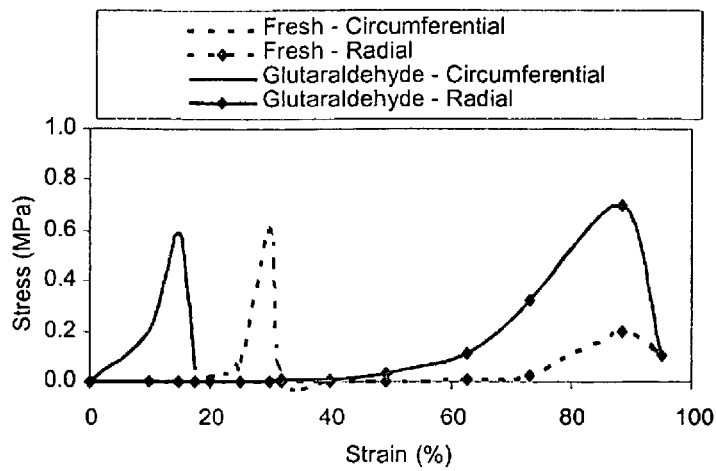
FIG. 3A illustrates the circumferential and radial stress-strain profiles for fresh and glutaraldehyde-fixed porcine aortic cusp tissues.
Figure 3B:
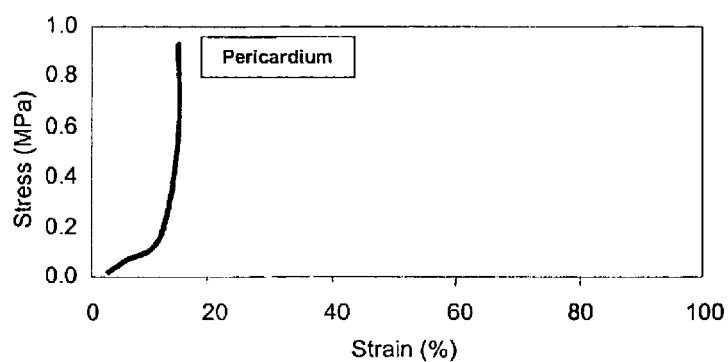
FIG. 3B illustrates the stress-strain profile for glutaraldehyde-fixed pericardial tissue over the same ranges as shown in FIG. 3A.

Porcine vena cava tissue, porcine aortic cusps, and bovine pericardial tissue were prepared and subjected to stress/strain tests as disclosed above in Example 1. FIG. 3A sets forth stress/strain data obtained for both GA-fixed and fresh porcine aortic cusps in both the radial and circumferential directions. The circumferential direction of an individual cusp runs parallel to the aortic wall, and the radial direction runs from the center of the cusp to the edge of the aorta. FIG. 3B sets forth the data obtained for GA-fixed pericardium, and FIG. 3C sets forth the data obtained for GA-fixed porcine vena cava in both the longitudinal (with blood flow) direction and circumferential (perpendicular to blood flow) direction.

Figure 3C:
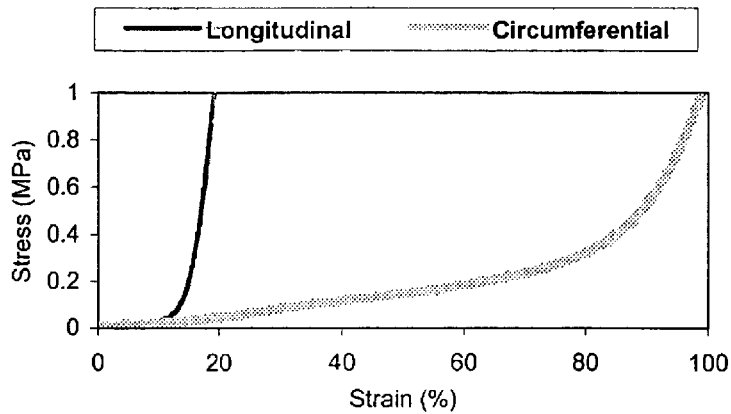
FIG. 3C illustrates the stress-strain profile for glutaraldehyde-fixed porcine vena cava tissue over the same range as shown in FIGS. 3A and 3B.

As seen in reference to FIG. 3C, GA-fixed vena cava is anisotropic, exhibiting greater elasticity in the circumferential direction than in the longitudinal direction. Further, in comparison to pericardial tissue (FIG. 3B), the vena cava biomaterial is significantly more extensible in both longitudinal and circumferential directions.

As discussed above in regard to FIG. 4, in one embodiment of the disclosed invention, individual BHV leaflets can be excised from vena cava tissue with the circumferential direction of the vein substantially corresponding to the radial direction of the prepared leaflet, and the longitudinal direction of the vein substantially corresponding to the circumferential direction of the prepared leaflet. As seen in comparison of FIGS. 3A and 3C, vena cava oriented in a longitudinal direction was found to be more elastic than GA-fixed aortic cusps in their circumferential direction. Vena cava tested in the circumferential direction is also more elastic than aortic cusps in the radial direction.

At the conclusion of the stress-strain tests, aortic cusps ruptured at around 1 MPa, while vena cava was able to withstand stresses higher than 5 MPa, as shown in FIG. 1. The data provided suggests that vena cava tissue has great strength and beneficial elasticity properties. Such properties may be used to advantage in the construction of a bioprosthetic heart valve.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed is:

1. A process for forming a bioprosthesis comprising:
   excising a tissue having an elastin content greater than about 10% by weight, wherein the tissue is vena cava tissue;
   forming the excised tissue into the shape of a heart valve leaflet; and
   attaching the heart valve leaflet to a support material of the bioprosthesis, wherein the support material is a heart valve stent or a suture ring.

2. The process of claim 1, wherein the tissue is an anisotropic material.

3. The process of claim 1, wherein the excised tissue is formed into the shape of a tricuspid valve leaflet.

4. The process of claim 1, wherein the excised tissue is formed into the shape of a bicuspid valve leaflet.

5. The process of claim 1, further comprising excising a section of vena cava, the vena cava section defining a longitudinal direction and a circumferential direction, and opening the section of vena cava with a longitudinal incision, wherein the opened section of vena cava is the vena cava tissue.

6. The process of claim 1, wherein the vena cava tissue is porcine vena cava tissue.

7. The process of claim 1, further comprising chemically fixing the tissue.

8. The process of claim 1, wherein the excised vena cava tissue has an elastin content greater than about 30% by weight.

* * * * *

UNITED STATES PATENT AND TRADEMARK OFFICE
CERTIFICATE OF CORRECTION

| | | |
|---|---|---|
| PATENT NO. | : 7,753,840 B2 | Page 1 of 1 |
| APPLICATION NO. | : 11/515963 | |
| DATED | : July 13, 2010 | |
| INVENTOR(S) | : Dan T. Simionescu and Narendra Vyavahare | |

It is certified that error appears in the above-identified patent and that said Letters Patent is hereby corrected as shown below:

Specification

Column 1, lines 16 - 18 states,

"The United States Government may have rights in this invention pursuant to Grant No. HL 61652 between Clemson University and the National Institutes of Health."

Please correct this paragraph to read as follows:

-- The United States Government has rights in this invention pursuant to Grant No. HL 61652 between Clemson University and the National Institutes of Health. --

Signed and Sealed this
Fifth Day of January, 2016

Michelle K. Lee
*Director of the United States Patent and Trademark Office*